United States Patent
Joy et al.

[11] Patent Number: 5,720,712
[45] Date of Patent: Feb. 24, 1998

[54] REUSABLE LIMB PROTECTOR

[76] Inventors: Dave A. Joy, 1660 Brenda Rd., Rio Rancho, N. Mex. 87124; Robert B. Gordon, 7401 San Pedro, N.E., No. 233, Albuquerque, N. Mex. 87109

[21] Appl. No.: 590,015

[22] Filed: Jun. 16, 1995

Related U.S. Application Data

[63] Continuation of Ser. No. 173,183, Dec. 23, 1993, abandoned.

[51] Int. Cl.$^6$ .............................................. A61F 5/00
[52] U.S. Cl. .................................. 602/3; 128/856
[58] Field of Search .................................. 602/3, 20, 23; 128/846, 849, 856; 2/16, 22, 26

[56] References Cited

U.S. PATENT DOCUMENTS

| | | | |
|---|---|---|---|
| 1,980,486 | 11/1934 | King et al. | 128/882 X |
| 3,329,144 | 7/1967 | Liman | 602/3 |
| 3,802,424 | 4/1974 | Newell | 602/3 |
| 4,036,220 | 7/1977 | Bellasalma | 602/3 |
| 4,178,924 | 12/1979 | Baxter . | |
| 4,254,765 | 3/1981 | Brown et al. . | |
| 4,346,699 | 8/1982 | Little et al. | 602/3 |
| 4,363,317 | 12/1982 | Broucek | 602/3 |
| 4,523,586 | 6/1985 | Couri . | |
| 4,562,834 | 1/1986 | Bates et al. | 602/3 |
| 4,610,245 | 9/1986 | Biearman . | |
| 4,966,135 | 10/1990 | Renfrew | 602/3 |
| 4,986,265 | 1/1991 | Caponi . | |
| 5,063,919 | 11/1991 | Silverberg . | |
| 5,083,557 | 1/1992 | Lennon et al. . | |

FOREIGN PATENT DOCUMENTS

| | | | |
|---|---|---|---|
| 2630908 | 11/1989 | France | 602/3 |

*Primary Examiner*—Linda C. Dvorak

[57] ABSTRACT

The present invention relates to a re-useable limb protector for use in protecting a limb with a cast or bandage. The limb protector is comprised of stretchable moisture impervious material which is adjustable in size to accommodate a wide range of individuals. The limb protector is constructed to be readily adaptable to either right- or left-handed individuals and is molded of a single piece of skid retardant material. The water tight seal is accomplished by stretching the moisture impervious base unit and is locked in place by the folding over of the two locking straps. The invention of a reuseable limb protector which does not require the use of an encircling mechanism to acheive a water tight seal is designed herein to allow for a normal blood flow when a water tight seal is acheived. The open end of the base unit is designed to be of a sufficient diameter to prevent irritation to sensitive finger and toe areas which would be caused by a need to stretch open the base unit for insertion of a limb.

20 Claims, 2 Drawing Sheets

REUSABLE LIMB PROTECTOR

This application is a continuation of application Ser. No. 08/173,183 filed Dec. 23, 1993, now abandoned.

BACKGROUND OF THE INVENTION

1. Field of the Invention (Technical Field)

This invention relates to a limb protector and more particularly to a protective cover for a cast or bandage on a limb, especially from moisture while bathing.

2. Background Art

At the present time, patients with casts or bandages find it difficult to protect the casts and bandages when taking showers or bathing. The most common form of protection in these instances are plastic garbage bags wrapped around the casts or bandages and then taped into place. The use of such plastic garbage bags is not without disadvantages. First, because they are normally much too large for the limb to be protected, there is an excess of material which can interfere with walking. Second, the garbage bags do not provide good traction therefore the user is at risk of slipping and falling and complicating the injury. Third, it is difficult to fasten the bag securely to form a water tight seal between the garbage bag and the injured limb.

Typical of the devices heretofore proposed are those disclosed in Lennon, et al., U.S. Pat. No. 5,083,557; Silverberg, U.S. Pat. No. 5,063,919; Caponi, U.S. Pat. No. 4,986,265; Biearman, U.S. Pat. No. 4,610,245; Couri, U.S. Pat. No. 4,523,586; Brown, et al., U.S. Pat. No. 4,254,765; and Baxter, U.S. Pat. No. 4,178,924.

The Lennon, et al., U.S. Pat. No. 5,083,557 describes a disposable unit which is not adjustable and non-reusable. This device is a two piece base unit which is then heat sealed together causing concerns regarding the consistency of this seal. This devices is specifically for foot injuries.

The Silverberg, U.S. Pat. No. 5,063,919 describes a device which uses a stretchable strap mechanism which encircles the limb to be protected which in the case of a good seal causes a restriction of blood flow. In order to avoid this problem, the stretchable strap must be loosely applied which creates a poor seal and therefore renders the device useless. The devices described in the U.S. Patents of Caponi, Biearman, Couri, Brown, et al., and Baxter all describe strap mechanisms which also encircle the limb and therefore suffer from the same deficiency as the Silverberg patent.

SUMMARY OF THE INVENTION
(DISCLOSURE OF THE INVENTION)

In accordance with the present invention there is disclosed a reusable limb protector that accommodates all sized limbs and is constructed for right or left handed use. The apparatus of the invention comprises a reusable protective cover for a limb comprising a molded cylindrical base unit comprising a unitary elastic and fluid impervious material with a first closed end, a fastening structure comprising at least two straps for right or left handed fastening to the base unit molded as part of the base unit, and a second end of the base unit comprising an opening for insertion of the limb.

The preferred unitary elastic and fluid impervious material comprises latex. The preferred unitary elastic and fluid impervious material also comprises a thickness sufficient for reuse of the protective cover.

The preferred at least two straps for right or left handed fastening to the base unit comprises hook and loop fasteners. The at least two straps also comprise the fasteners affixed to each side of the at least two straps and on at least two predetermined locations on the base unit. The at least two straps for right or left handed fastening to the base unit further comprises a first and second strap wherein the first strap is located substantially at the second end of the base unit and the second strap is located substantially one-half of a distance between the first strap and the first end of the base unit.

The preferred fastening structure comprises a first fastening element affixed to either side of the first and second strap, and a second fastening element affixed to the base unit adjacent to either side of the first and second strap whereby the fastening elements are of a length to accommodate different size limbs.

The preferred leg cover embodiment comprises the first closed end of the base unit comprises a boot member. The preferred boot member comprises a one end closed tubular cover with an open end affixed perpendicularly to the base unit at the first end.

The preferred material further comprises a skid retardant material.

A primary object of the present invention is to provide a limb protector whose water tight seal is created by the device rather than an encircling strap.

Yet another object of the present invention is to provide a limb protector that is useable by either left- or right-handed persons.

A primary advantage of the present invention is that it does not require different sizes for patients, therefore it is available to most patients no matter their size.

Another advantage of the present invention is that it is reusable, adjustable in height and width, provides superior traction and would be easy to use by either left- or right-handed individuals.

Yet another advantage of the present device is that it is easy to put on and remove due to its single piece construction.

Yet another advantage is that the cost to manufacture is reduced due to the need for fewer sizes and the single piece mold process.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings.

DESCRIPTION OF THE PREFERRED EMBODIMENTS (BEST MODES FOR CARRYING OUT THE INVENTION)

Figure 1:
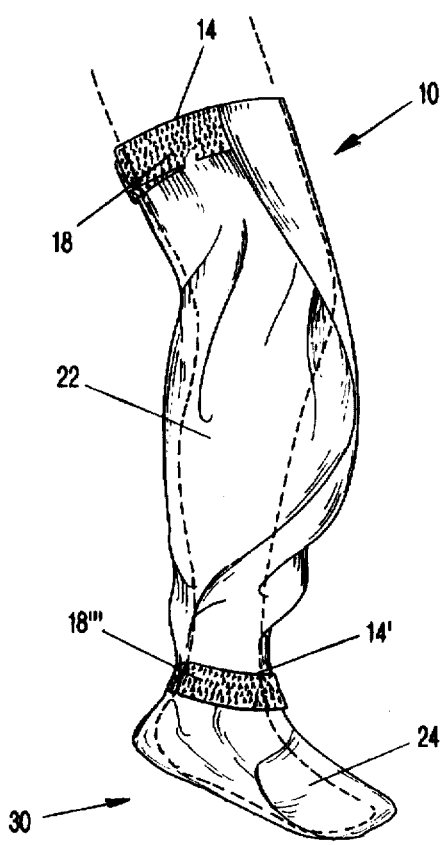
FIG. 1 is a side perspective view of the preferred leg cover of the present invention applied on a persons leg.
Figure 2:
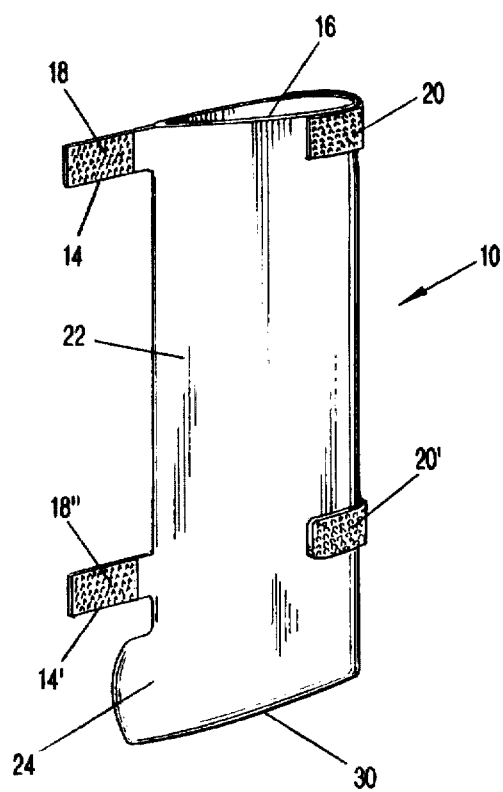
FIG. 2 is a perspective side view of the preferred leg cover.
Figure 3:
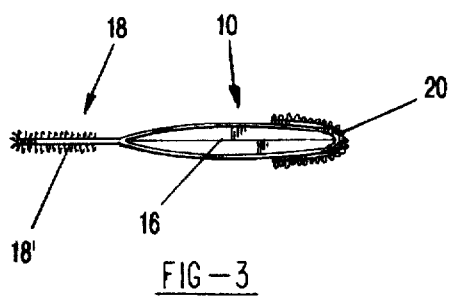
FIG. 3 is top view of the leg cover of FIG. 2.
Figure 4:
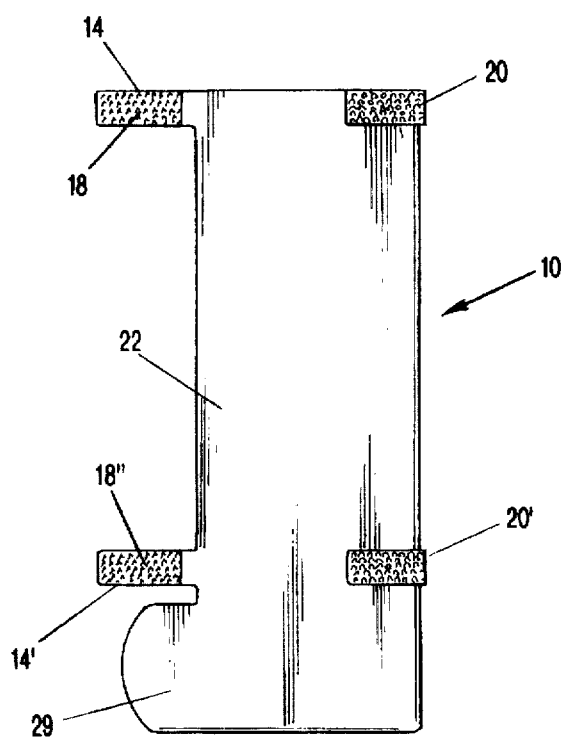
FIG. 4 is left side view of the leg cover of FIG. 2, the right side being a mirror image thereof.
Figure 5:
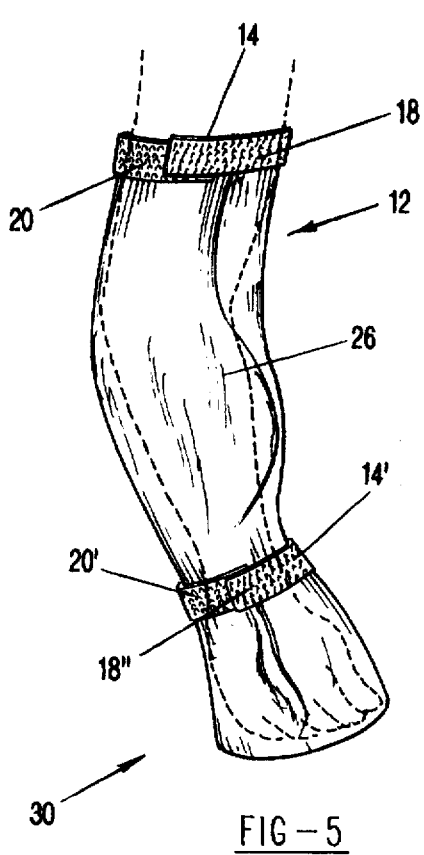
FIG. 5 is a side perspective view of the preferred arm cover of the present invention applied an a persons arms.
Figure 6:
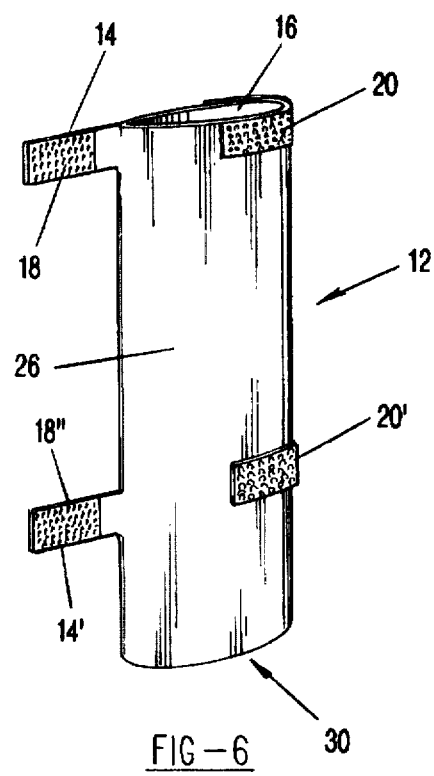
FIG. 6 is a perspective side view of the preferred arm cover.
Figure 7:
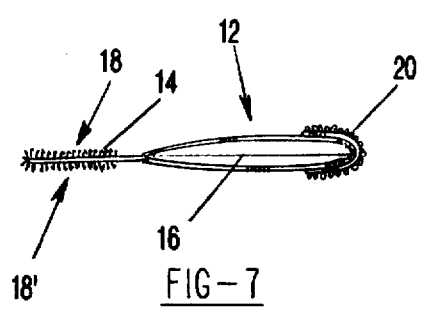
FIG. 7 is a top view of the arm cover of FIG. 6.
Figure 8:
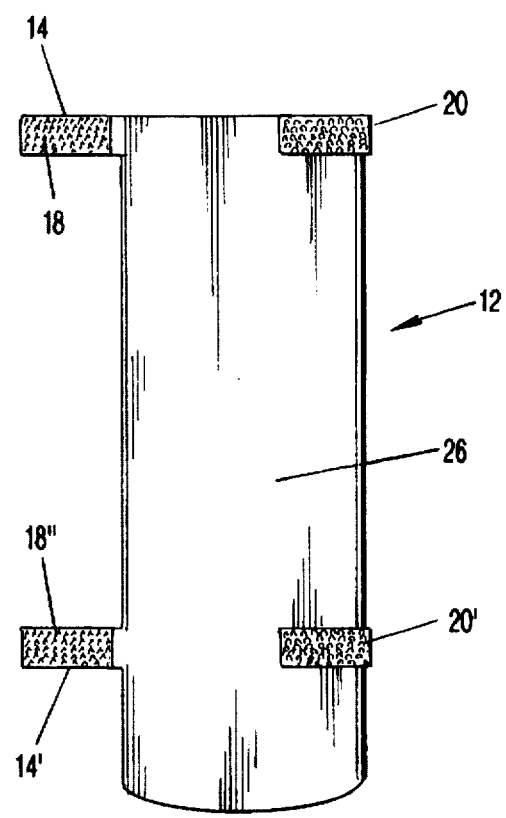
FIG. 8 is a left side view of the arm cover of FIG. 6, the right side being a mirror image thereof.

In the preferred embodiment of the invention shown in FIGS. 1 through 8, the preferred protective cover (leg cover 10 and arm cover 12) is preferably constructed from a single piece molded sleeve made of stretchable material such as latex. Covers 10 and 12 are constructed to a thickness which allows for elasticity and the ability to re-use at the same time. Tab 14 is preferably located at top of the open end 6 and tab 14' is preferably located one-half the distance from tab 14 to closed end 30 as shown. Tabs 14 and 14' are an integral part of the single piece design as shown in FIGS. 3 and 7 and are molded as part of the base cover 10 and 12. Tabs 14 and 14' are constructed and placed on cover 10 and 12 for left or right handed use.

Tabs 14 and 14' preferably comprise four separate equal lengths of male fastening hook and loop material 18, 18', 18" and 8'", or can comprise two lengths of male hook and loop material overlapping tabs 14 and 14'. These lengths 18–8'" are affixed to both sides of tabs 14 and 14' with a pressure sensitive adhesive or other similar method, all which are well known in the art. The attachment of material 18–18'" to both sides of tabs 14 and 14' allows for left or right handed use.

Female fastening hook and loop material 20 and 20' are affixed to base unit 10 and 12 in such a manner that they wrap around back of base unit 22 to points on both sides of the base unit 10 and 12 that are equally distant from male hook and loop locking straps 18–18'" and can be fastened around different diameter limbs (not shown). Material 20 and 20' is also affixed to base unit 10 and 12 by a pressure sensitive adhesive, or the like and positioned for right or left handed use.

Base unit 10, is constructed for use on legs. As shown in FIGS. 1–4 cylindrical section 22 comprises material of sufficient open diameter to cover most leg and cast sizes. The preferred open diameter for leg unit is 12 inches, however other diameters can be utilized. Boot section 24 of leg unit 10 is part of base unit 10, molded to bottom end 30 of base unit 10. Boot section 24 is molded to encase most feet and casts, however the preferred length of boot section 24 is approximately 3 inches from the end of cylindrical section 22 and the preferred diameter of boot section 24 is approximately 7 inches.

The preferred embodiment of arm unit 2 is shown in FIGS. 5–8. Arm unit 12 comprises cylindrical portion 26 with open end 16 for insertion of an arm or casted arm. Cylindrical portion 26 has an open diameter to encase most arms and arm casts, with the preferred open diameter of cylindrical portion 26 being approximately 8 inches. The length of base unit 12 is sufficient to cover most arms and arm casts with the preferred length being approximately 22 inches.

Base units 10 and 12 are constructed of stretchable latex, or the like, which is pulled to remove the slack material and apply tension. Excess material is then folded over and locked in place by virtue of locking straps 18–18'". This allows the water tight seal to be formed thereby distributing the tension of the water tight seal throughout the device which does not cause a restriction of blood flow.

The preferred method of putting on the cast protector is to insert the limb or casted limb into the unit 10 or 12. Lower seal 14 is completed first, then upper seal 14' is fastened which comprises a water tight seal. Excess material is billowed between locking straps 14 and 14', allowing for use with different length limbs or casted limbs. The diameter of base units 10 and 12 are adjustable by overlapping excess material when fastening straps 14 and 14'. By virtue of the adjustability in both length and diameter, the present invention may be used on many different individuals of differing sizes. This feature, when combined with the single piece molding process, ensures inexpensive manufacturing costs and ease of issuing to patients without sizing difficulties.

Both base units 10 and 12 are preferably made from latex, or the like of sufficient thickness (mil thickness) so they can be re-used by the patient or by a variety of different patients following a sterilization procedure between patients. In addition, material such as latex are preferred for their slip resistant qualities which is of paramount importance especially for the leg cover embodiment FIGS. 1–4 for walking casts and the like.

What is claimed is:

1. A reusable protective cover for a limb comprising:
   a molded cylindrical base unit comprising a unitary elastic and fluid impervious material with a first closed end;

a second end of said base unit comprising an opening for insertion of the limb; and a fastening means comprising at least two straps for right or left handed fastening to said base unit, said two straps being molded as part of said base unit;

wherein each of said at least two straps comprises first and second fasteners, said first fastener being located at the outermost end of each strap and a second fastener also located at the outermost end of each strap and positioned on the reverse side opposite said first fastener location.

2. The invention of claim 1 wherein said unitary elastic and fluid impervious material comprises latex.

3. The invention of claim 1 wherein said unitary elastic and fluid impervious material comprises a thickness sufficient for reuse of said protective cover.

4. The invention claim 1 wherein said at least two straps for right or left handed fastening to said base unit comprises hook and loop fasteners.

5. The invention of claim 1 wherein said at least two straps for right or left handed fastening to said base unit comprises a first and second strap means wherein said first strap means is located substantially at said second end of said base unit and said second strap means is located substantially one-half of a distance between said first strap means and said first end of said base unit.

6. The invention of claim 1 wherein said first closed end of said base unit comprises a boot member.

7. The invention of claim 6 wherein said boot member comprises a one end closed tubular cover with an open end affixed perpendicularly to said base unit at said first end.

8. The invention of claim 1 wherein said material comprises a skid retardant material.

9. The invention of claim 1 wherein said fastening means distributes the tension created by a water tight seal throughout said base unit.

10. The invention of claim 1 wherein the at least two straps for right or left handed fastening are used as a means to lock in place the already existing water tight seal created by said base unit.

11. The invention of claim 1 wherein said base unit folds over flatly against itself to eliminate bunching of material and the creation of water pathways.

12. The invention of claim 1 wherin the second end of said base unit comprises an opening of sufficient diameter to allow for the insertion of a limb of varying sizes.

13. A reuseable protective cover for a limb comprising:
- a generally tubular sleeve comprising a flexible, elastic and fluid impervious material with a first closed end;
- a second open end comprising an opening for insertion of the limb;
- the sleeve being molded into a flat configuration in which opposite side edges are defined longitudinally of the sleeve;
- the sleeve being provided with two non-encircling locking tabs which are incapable in length of encircling the limb, the first being located at the extreme outermost end of the second open end and the second being positioned substantially anywhere along the mid length of the sleeve;
- each said locking tab having a first fastener on its outermost end and a second fastener positioned on the reverse side of said locking tab opposite said first fastener location;
- the sleeve being provided with two receiving pads which are positioned at the directly opposing side of the sleeve from the locking tabs for receiving either of said first or second fasteners of said locking tabs.

14. The invention of claim 13 wherein the flexible, elastic and fluid impervious material of the sleeve is capable of stretching a sufficient distance that the stretch tight seal may be held in place while the locking tabs are folded over to be received by the locking pads.

15. The invention of claim 13 wherein the locking tabs and pads are locked together through use of hook and loop fastening means.

16. The invention of claim 15 wherein said hook and loop material is positioned substantially similar distances along the sleeve on both sides of the flat molded sleeve.

17. The invention of claim 13 wherein said flexible, elastic and fluid impervious material comprises a thickness sufficient for reuse of said protective cover.

18. The invention of claim 13 wherein said flexible, elastic and fluid impervious material comprises latex.

19. The invention of claim 13 wherein the first closed end is chemically roughened to provide a non-skid surface.

20. The invention of claim 13 wherein one of the at least two non-encircling straps are the means to lock the pre-existing water tight seal in place:
- a non-encircling strap located at the outermost end of the second open end (16) as a means of locking in place a water tight seal without encircling and being incapable of encircling the limb or base unit (22).

* * * * *